United States Patent
Sharpe, Jr. et al.

(10) Patent No.: US 9,310,288 B2
(45) Date of Patent: Apr. 12, 2016

(54) SYSTEMS AND METHODS TO MONITOR OPERATING PROCESSES

(71) Applicant: Fisher-Rosemount Systems, Inc., Round Rock, TX (US)

(72) Inventors: Joseph Hiserodt Sharpe, Jr., Glen Allen, VA (US); Hallgeir Jenssen, Trondheim (NO)

(73) Assignee: FISHER-ROSEMOUNT SYSTEMS, INC., Round Rock, TX (US)

(*) Notice: Subject to any disclaimer, the term of this patent is extended or adjusted under 35 U.S.C. 154(b) by 192 days.

(21) Appl. No.: 13/751,970

(22) Filed: Jan. 28, 2013

(65) Prior Publication Data

US 2014/0212978 A1    Jul. 31, 2014

(51) Int. Cl.
*G01N 17/00* (2006.01)
*G05B 23/02* (2006.01)
*G01N 33/28* (2006.01)

(52) U.S. Cl.
CPC ............ *G01N 17/00* (2013.01); *G05B 23/0235* (2013.01); *G05B 23/0272* (2013.01); *G01N 33/2823* (2013.01)

(58) Field of Classification Search
CPC ..................................................... G01N 17/00
USPC ............ 436/6, 50, 55, 61, 121, 163; 700/266, 700/271, 272; 702/30–31
See application file for complete search history.

(56) References Cited

U.S. PATENT DOCUMENTS

| | | | | |
|---|---|---|---|---|
| 4,020,488 A | * | 4/1977 | Martin et al. | 340/508 |
| 4,353,257 A | * | 10/1982 | Vrba et al. | 73/623 |
| 4,599,217 A | * | 7/1986 | Winston et al. | 422/53 |
| 4,658,365 A | * | 4/1987 | Syrett et al. | 205/724 |
| 4,953,147 A | * | 8/1990 | Cobb | 367/35 |
| 5,332,900 A | * | 7/1994 | Witzke et al. | 250/341.1 |
| 5,352,351 A | * | 10/1994 | White et al. | 204/403.04 |
| 5,438,271 A | * | 8/1995 | White et al. | 324/444 |
| 6,000,277 A | * | 12/1999 | Smith et al. | 73/37 |
| 6,294,387 B1 | * | 9/2001 | Yepez et al. | 436/6 |
| 6,336,058 B1 | * | 1/2002 | Fowee | 700/266 |
| 6,385,552 B1 | * | 5/2002 | Snyder | 702/123 |
| 6,591,166 B1 | * | 7/2003 | Millett et al. | 700/266 |

(Continued)

FOREIGN PATENT DOCUMENTS

| | | |
|---|---|---|
| CN | 102855368 A | 1/2013 |
| WO | 2007038533 A2 | 4/2007 |

OTHER PUBLICATIONS

Intellectual Property Office of Great Britain, "Search Report under Section 17(5)", issued in connection with British patent application No. GB1400507.8, mailed on Jul. 1, 2014, 4 pages.

*Primary Examiner* — Arlen Soderquist

(74) *Attorney, Agent, or Firm* — Hanley, Flight and Zimmerman, LLC

(57) ABSTRACT

Example methods, systems, and computer readable media are provided for monitoring operating processes. An example method includes monitoring an equipment parameter associated with an asset in an operating process unit and monitoring a process parameter associated with the asset. The example method includes determining an asset health corresponding to the asset. The asset health is determined based on a potential state of corrosion associated with the asset by comparing a corrosivity index to a corrosion threshold. The corrosivity index is a function of at least one of current values or changes in the monitored equipment parameter or the monitored process parameter over time.

23 Claims, 8 Drawing Sheets

(56) References Cited

U.S. PATENT DOCUMENTS

| | | | |
|---|---|---|---|
| 6,681,153 B1* | 1/2004 | Horn et al. | 700/286 |
| 6,772,082 B2* | 8/2004 | van der Geest et al. | 702/116 |
| 7,043,372 B2* | 5/2006 | Koehler et al. | 702/25 |
| 7,158,894 B2* | 1/2007 | Hatch | 702/30 |
| 7,160,728 B2* | 1/2007 | Chimenti et al. | 436/29 |
| 7,704,371 B2* | 4/2010 | Meyer et al. | 205/725 |
| 7,818,156 B2 | 10/2010 | Vachhani et al. | |
| 7,866,211 B2 | 1/2011 | Brown | |
| 7,955,853 B2* | 6/2011 | Hicks et al. | 436/6 |
| 7,982,474 B1 | 7/2011 | Hefner et al. | |
| 8,185,326 B2* | 5/2012 | Safai et al. | 702/30 |
| 8,280,554 B2* | 10/2012 | Bergman et al. | 700/271 |
| 2001/0047221 A1* | 11/2001 | Fowee | 700/202 |
| 2003/0005747 A1* | 1/2003 | van der Geest et al. | 73/1.16 |
| 2004/0106204 A1* | 6/2004 | Chimenti et al. | 436/55 |
| 2004/0166584 A1* | 8/2004 | Misra et al. | 436/164 |
| 2005/0010462 A1* | 1/2005 | Dausch et al. | 705/8 |
| 2005/0107963 A1 | 5/2005 | Campbell | |
| 2005/0148081 A1* | 7/2005 | Braunling et al. | 436/6 |
| 2005/0171703 A1* | 8/2005 | Goldfine et al. | 702/30 |
| 2006/0288756 A1* | 12/2006 | De Meurechy | 73/1.01 |
| 2007/0028663 A1* | 2/2007 | Patten et al. | 73/1.34 |
| 2007/0055392 A1* | 3/2007 | D'Amato et al. | 700/44 |
| 2007/0122911 A1* | 5/2007 | Browning et al. | 436/55 |
| 2007/0233397 A1* | 10/2007 | Kim | 702/19 |
| 2007/0239365 A1* | 10/2007 | Hanson et al. | 702/22 |
| 2007/0251461 A1* | 11/2007 | Reichard et al. | 119/245 |
| 2007/0257806 A1* | 11/2007 | Madden et al. | 340/603 |
| 2008/0262795 A1* | 10/2008 | Webb et al. | 702/184 |
| 2009/0030553 A1* | 1/2009 | Hicks et al. | 700/266 |
| 2009/0035180 A1* | 2/2009 | Wan et al. | 422/62 |
| 2009/0065439 A1* | 3/2009 | Hicks et al. | 210/696 |
| 2009/0125127 A1* | 5/2009 | Bergman et al. | 700/80 |
| 2009/0319084 A1* | 12/2009 | Kane et al. | 700/266 |
| 2010/0023359 A1* | 1/2010 | Easo et al. | 705/7 |
| 2010/0099193 A1* | 4/2010 | Hsu et al. | 436/47 |
| 2010/0100404 A1* | 4/2010 | Hodges et al. | 705/7 |
| 2010/0217538 A1* | 8/2010 | Safai et al. | 702/30 |
| 2010/0332149 A1* | 12/2010 | Scholpp | 702/25 |
| 2011/0223672 A1* | 9/2011 | Tumiatti et al. | 436/6 |
| 2012/0128469 A1* | 5/2012 | Kato et al. | 415/118 |
| 2012/0142113 A1* | 6/2012 | Banks et al. | 436/43 |
| 2012/0150451 A1* | 6/2012 | Skinner et al. | 702/24 |
| 2012/0160707 A1* | 6/2012 | Kusinski et al. | 205/775 |
| 2013/0024026 A1* | 1/2013 | Prasad et al. | 700/272 |
| 2013/0047613 A1* | 2/2013 | Holt et al. | 60/645 |
| 2013/0176418 A1* | 7/2013 | Pandey et al. | 348/83 |
| 2013/0236975 A1* | 9/2013 | Roumeau et al. | 436/6 |
| 2013/0289320 A1* | 10/2013 | Barney et al. | 585/3 |
| 2014/0004619 A1* | 1/2014 | Caseres et al. | 436/163 |
| 2014/0080172 A1* | 3/2014 | Tunheim et al. | 435/34 |

* cited by examiner

SYSTEMS AND METHODS TO MONITOR OPERATING PROCESSES

FIELD OF THE DISCLOSURE

This disclosure relates generally to operating processes and, more particularly, to systems and methods to monitor operating processes.

BACKGROUND

Process operations, like those used in the oil and gas production industries, refining industries, petrochemical industries, etc., typically include significant equipment assets, such as pumps, heat exchangers, cooling towers, pipes, vessels, etc. The condition, health, integrity, and/or performance of such assets are essential to the efficiency and/or safety of processing plants.

SUMMARY

Example methods, systems, and computer readable media are provided for monitoring operating processes. An example method includes monitoring an equipment parameter associated with an asset in an operating process unit and monitoring a process parameter associated with the asset. The example method includes determining an asset health corresponding to the asset. The asset health is determined based on a potential state of corrosion associated with the asset by comparing a corrosivity index to a corrosion threshold. The corrosivity index is a function of at least one of current values or changes in the monitored equipment parameter or the process parameter over time.

An example system includes a monitoring application to monitor an equipment parameter and a process parameter associated with an asset in a process unit. The example system includes an asset health value calculator to determine an asset health corresponding to the asset. The asset health being determined based on thermal stress associated with the asset by comparing a thermal stress index to a thermal stress threshold. The thermal stress index is a function of changes of the monitored equipment parameter or the process parameter over time.

An example tangible computer readable storage medium comprises instructions that, when executed, cause a computing device to monitor an equipment parameter associated with an asset in an operating process unit and to monitor a process parameter associated with the asset. The example instructions cause the computing device to determine an asset health corresponding to the asset. The asset health is determined based on a potential state of corrosion associated with the asset by comparing a corrosivity index to a corrosion threshold. The corrosivity index is a function of at least one of current values or changes in the monitored equipment parameter or the process parameter over time.

DETAILED DESCRIPTION

Figure 1:
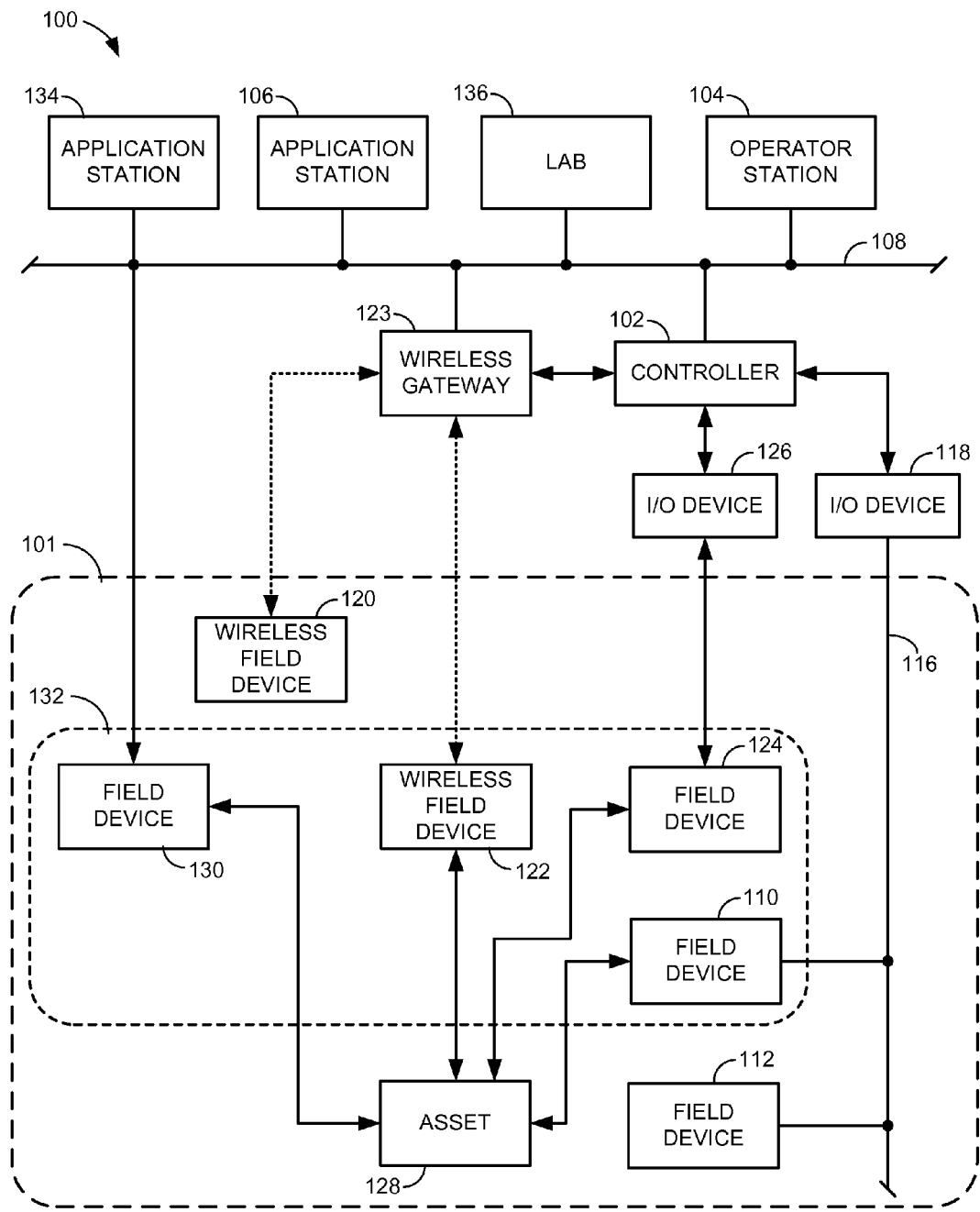
FIG. 1 is a schematic illustration of an example operating process unit within which the teachings of this disclosure may be implemented.

Industry averages suggest that roughly five percent of production capacity is lost each year due to unplanned downtime. One of the most significant causes for such downtime is equipment failure, which can often exceed forty percent of unplanned downtime. Not only can an unexpected failure lead to lost production and increased maintenance costs, in some circumstances, an equipment failure may raise safety concerns. While some operating process units may monitor the most critical equipment by using sensors that communicate with a host system, it is often cost prohibitive to monitor all assets online and/or in real-time. Accordingly, the remaining equipment is manually checked through clipboard walkarounds and periodic handheld measurement and monitoring devices to obtain isolated data concerning the condition, health, integrity and/or performance of the equipment or asset. The result of this manual approach is that many assets within an operating process unit are operating without being monitored most of the time, thereby increasing the risk of equipment failures and/or other undesirable impacts on the performance and/or safety of the entire system.

Corrosion is an example factor to be monitored as corrosion may cause equipment failure (e.g., failure of pipes, vessels, valves, steam systems, boilers, steam drums, etc.) in many production facilities, refineries, piping systems, etc. Indeed, corrosion monitoring, control, and/or abatement represent large costs for many industries. Corrosion is a gradual destruction of materials (e.g., metals) due to, for example, a chemical reaction with an environment. Rusting is a common form of corrosion. Corrosion may degrade properties of the materials and adversely affect strength of the materials and/or permeability of the materials to liquids and/or gases. For example, chemical-based corrosion of piping materials may result in leaks. Corrosion affects most types of metal alloys and occurs at different rates, often depending on the particular metal alloy and the environment in which the metal alloy is used.

Thermal stress may also cause equipment failure (e.g., failure of pipes, vessels, valves, furnace tubes, steam systems, boilers, steam drums, etc.) in many production facilities, refineries, piping systems, etc. Thermal stress may degrade materials and adversely affect strength of the materials and/or permeability of the materials to liquids and/or gases due to excessive and/or extreme temperature changes. Thermal stress may occur when, for example, a large temperature change repeatedly occurs over a small period of time. In some examples, thermal stress may be a form of corrosion caused by rapid temperature change or a large temperature gradient that may cause cracks to form in materials.

Standards (e.g., those provided by the National Association of Corrosion Engineers ("NACE")) are often applied in production environments to specify limits on wall or pipe thickness, operating pressures, temperatures, etc. for different materials and/or schedules to avoid damage and/or problems caused by corrosion. Owners and/or operators of the production environments may specify safety margins, operating limits, inspection parameters, etc. and inspect the production environments to determine when to replace equipment and/or production components (e.g., piping segments).

Devices may be used to periodically (e.g., monthly) measure material loss and/or wall thickness to detect corrosion. However, since corrosion occurs over a period of time (e.g., not instantaneously), the devices are not typically monitored and/or alarmed in a control system in real time (or substantially real time). Accordingly, existing corrosion monitoring systems focus on long-term corrosion measurement trends to determine if and/or when inspection or repair is required. Corrosion monitoring systems that combine process data, analytical data, corrosion data, etc. to perform a comprehensive corrosion analysis that provides an indication of corrosion before degradation of an asset occurs are currently not available.

Examples disclosed herein recognize that while deterioration of materials due to corrosion occurs over a period of time, many operating and/or process conditions that lead to corrosion occur over a shorter period of time (e.g., shorter than the time period to detect metal deterioration). For example, production environments extending beyond preferred operating limits with operating conditions related to flow rates, sulfur amounts, chloride amounts, acid amounts, temperatures, pressures, chemical compositions (e.g., pH levels), etc. may lead to corrosion in the production environments. Monitoring operating conditions in real time to determine when assets are operating in a corrosive region may lead to early detection of production environments prone to corrosion before degrading assets and/or before such corrosion may be detected with previous systems. Early detection of corrosive environments (e.g., potential states of corrosion) reduces maintenance cost and/or process impact.

Avoiding equipment damage, environmental incidents, and/or negative impacts on business as described above depends on being able to detect changes in process variables and/or equipment conditions as they occur (i.e., in substantially real-time via online monitoring). Furthermore, being able to relate multiple measurements provides greater predictive value in assessing the likelihood of the onset of asset failures (e.g., due to chemical-based corrosion and/or thermal stress) as it provides a more complete picture of the condition of the asset. Thus, even where individual measurements on a particular piece of equipment are collected, the engineer collecting the measurements is unlikely to appreciate the significance of the individual measurements in light of other parameters associated with the asset. For example, devices may be used to periodically measure material loss and/or wall thickness to detect corrosion (e.g., monthly). However, since corrosion generally occurs over a period of time (e.g., not instantaneously), the devices are not typically monitored and/or alarmed in a control system in real time (or substantially real time) and may not detect operating conditions that occur over a shorter period of time that may lead to corrosion. Without having all this information available and properly understood, these individual measurements will have less value in determining the present health of the asset and/or anticipating impending failures than when multiple measurements are integrated into a comprehensive view of the overall condition of the asset.

Examples disclosed herein recognize that, while there are many potential causes of equipment failures (e.g., chemical-based corrosion and/or thermal stress), and provide a method that combines specific equipment health measurements with process measurements (e.g., corrosion and/or thermal stress measurements) to make a more sophisticated or integrated analysis of what might be occurring. Using this integrated analysis, the example system and methods disclosed herein enable the determination of an overall asset health status or value and the identification of the most critical parameters affecting the condition of an asset to an operator, engineer, maintenance staff, and/or other plant personnel (hereinafter collectively referred to as an operator). In some examples, using this integrated analysis, the example systems and methods disclosed herein enable the determination of a potentially corrosive state of an asset (e.g., a pipe and/or vessel) and/or thermal stress at the asset, and the identification of the most critical parameters affecting the condition of the asset (e.g., temperature, pressure, pH level, conductivity, etc.) to an operator. Furthermore, the examples disclosed herein involve systems and methods that provide an earlier detection of potential asset failures (e.g., due to corrosion and/or thermal stress) than previous systems by integrating measurements that are sensitive to likely failure modes, including both equipment and process data (e.g., temperature, pH, conductivity, wall thickness, etc.), analysis of the combined or integrated information to produce an overall indication of the likelihood of a near term failure, and presentation to operators in a manner that permits them to quickly understand the state of the asset and the possible failure.

FIG. 1 is a schematic illustration of an example system 100 implementing an operating process unit 101 in accordance with the teachings of this disclosure. Accordingly, while the teachings of this disclosure may be implemented in connection with a process control system (e.g., via the example controller 102), the teachings of this disclosure may also be implemented completely independent of a process control system. The example system 100 may be a distributed control system (DCS), a supervisory control and data acquisition (SCADA) system and/or any other type of process system that monitors and/or controls the example operating process unit 101. Additionally or alternatively, the example operating process unit 101 may be monitored and/or associated with an asset management system (AMS) regardless of whether the system 100 is providing any control of the operating process unit 101. As illustrated in FIG. 1, the example system 100 includes one or more process controllers (one of which is designated at reference numeral 102), one or more operator stations (one of which is designated at reference numeral 104), and one or more application stations (one of which is designated at reference numeral 106). The example process controller 102, the example operator station 104 and the example application station 106 are communicatively coupled via a bus and/or local area network (LAN) 108, which is commonly referred to as an area control network (ACN).

The example LAN 108 of FIG. 1 may be implemented using any desired communication medium and protocol. For example, the example LAN 108 may be based on a hardwired and/or wireless Ethernet communication scheme. However, any other suitable communication medium(s) and/or protocol(s) could be used. Further, although a single LAN 108 is illustrated in FIG. 1, more than one LAN and/or other alternative communication hardware may be used to provide redundant communication paths between the example systems of FIG. 1.

The example operator station 104 of FIG. 1 allows an operator to review and/or operate one or more operator display screens and/or applications that enable the operator to view process control system variables, states, conditions, alarms; change process control system settings (e.g., set points, operating states, clear alarms, silence alarms, etc.); configure and/or calibrate devices within the operating process unit 101; perform diagnostics of devices within the operating process unit 101; and/or otherwise manage and interact with devices within the operating process unit 101.

The example application station 106 of FIG. 1 may be configured to perform one or more information technology applications, user-interactive applications and/or communication applications. For example, the application station 106 may be configured to perform primarily process control-related applications, while another application station (not shown) may be configured to perform primarily communication applications that enable the operating process unit 101 to communicate with other devices or systems using any desired communication media (e.g., wireless, hardwired, etc.) and protocols (e.g., HTTP, SOAP, OPC, Modbus, Foundation Fieldbus, etc.). In some examples, a remote session may be established on the example application station 106 to view and/or interact with the applications on the example operator station 104. Additionally, the example application station 106 and/or the example operator station 104 may include and/or implement an asset monitoring application (e.g., the example asset monitoring application of FIG. 3) that may be part of an asset management software (AMS) application. The asset monitoring application of the example application station 106 monitors data associated with an asset 128 and determines when the asset 128 is operating in a potentially corrosive environment and/or when the asset 128 is undergoing thermal stress. In the example of FIG. 1, the asset monitoring application is associated with a user interface (e.g., the example user interface of FIG. 3) to display information and/or provide visual indications of the condition, health, integrity, and/or performance of the asset 128 (e.g., related to chemical-based corrosion and/or thermal stress) within the operating process unit 101. An example manner of implementing the example application station 106 of FIG. 1 is described below in connection with FIG. 3.

The example operator station 104 and the example application station 106 of FIG. 1 may be implemented using one or more workstations and/or any other suitable computer systems and/or processing systems. For example, the operator station 104 and/or application station 106 could be implemented using single processor personal computers, single or multi-processor workstations, etc. Furthermore, the example operator station 104 and/or the application station 106 may connect to another network from which other users (e.g., maintenance and/or equipment engineers), via separate workstations, may have access. Additionally or alternatively, the example operating process unit 101 may contain other workstations within the same network (e.g., a maintenance station and/or an engineering station) to provide separate functionality associated with the operating process unit 101.

The example of FIG. 1 includes a laboratory 136 to facilitate automated and/or manual entry of measurements and/or values associated with the example system 100. In some examples, measurement devices may have manual operation (e.g., corrosion coupons may be removed from an asset and weighed). Data obtained from such measurement devices may be entered at the laboratory 136. Measurements and/or values automated and/or entered at the laboratory 136 are made available to the applications station 106 or other devices to facilitate asset monitoring.

The example controller 102 of FIG. 1 is coupled to a plurality of smart field devices 110, 112 via a data bus 116 and an input/output (I/O) device 118, such as an I/O card communicatively coupled to the controller 102. In some examples, the smart field devices 110, 112 may be Fieldbus compliant valves, actuators, sensors, etc., in which case the smart field devices 110, 112 communicate via the data bus 116 using the well-known Foundation Fieldbus protocol. Of course, other types of smart field devices and communication protocols could be used instead. For example, the smart field devices 110, 112 could instead be Profibus and/or HART compliant devices that communicate via the data bus 116 using the well-known Profibus and HART communication protocols. Additional I/O devices (similar and/or identical to the I/O device 118) may be coupled to the controller 102 to enable additional groups of smart field devices, which may be Foundation Fieldbus devices, HART devices, etc., to communicate with the controller 102.

As shown in the illustrated example, other smart field devices 120, 122 are wireless devices that relay data to a wireless gateway 123. In some such examples, the wireless gateway 123 interfaces with the controller 102 (e.g., via a wireless I/O card). Using such wireless technology enables the reduction in cost and complexity of wiring and configuring hardwired cables for each device. Additionally or alternatively, in some examples, the wireless gateway 123 connects directly to the ACN (e.g., the LAN 108) to enable transmitted data to be read directly by the application station 106 using Object Linking and Embedding (OLE) for Process Control (OPC).

In addition to the example smart field devices 110, 112, 120, 122 one or more non-smart field devices 124 may be communicatively coupled to the example controller 102. The example non-smart field devices 124 of FIG. 1 may be, for example, conventional 4-20 milliamp (mA) or 0-24 volts direct current (VDC) devices that communicate with the controller 102 via respective hardwired links connected to corresponding I/O cards (e.g., represented by the I/O device 126) associated with the controller 102.

In the example of FIG. 1, a smart field device 130 is communicatively coupled to an application station 134. The example application station 134 of FIG. 1 is similar to the example application station 106. The application station 134 may interpret signals received directly from the field device 130 and the application station 134 may make measurements associated with the field device 130 available to the application station 106 or other devices.

In the illustrated example of FIG. 1, at least some of the smart field devices 110, 122, 130 and/or the non-smart field devices 124 may be associated with the example asset 128 (e.g., a pipe and/or vessel) to monitor and/or control parameters associated with the asset 128 in the operating process unit 101. The asset 128 may be any asset within the example operating process unit 101 such as columns, drums, vessels, pipes, heat exchangers, separators, desalters, fired heaters, reactors, regenerators, boilers, steam headers, compressors, etc., or any combination thereof. In the illustrated example, the asset 128 is a unit including a plurality of pipes and vessels. In some examples, the field devices 110, 122, 124, 130 may be directly integrated with the asset 128. In other examples, the field devices 110, 122, 124, 130 may be separate devices that may be in communication with, or otherwise interact with, the asset 128. Furthermore, others of the field devices 112, 120 in the illustrated examples may be configured to monitor and/or control other components within the operating process unit 101. In some examples, the field devices 110, 122, 124, 130 are referred to generally as corrosion monitoring devices 132 and may be used to collect operating parameters and/or measurements related to determining corrosive states at the asset 128. Such measurements may include, for example, temperature, pH level, conductivity, sulfide amounts, steam flow, water flow, dew points, pressure, pipe hammer, material thickness, etc. The corrosion monitoring devices 132 may be implemented using specialized computers and/or software, rather than traditional I/O cards (e.g., a DeltaV I/O card).

The example controller 102 of FIG. 1 may be, for example, a DeltaV™ controller sold by Fisher-Rosemount Systems, Inc., an Emerson Process Management company. However, any other controller could be used instead. Further, while only one controller 102 is shown in FIG. 1, additional controllers and/or process control platforms of any desired type and/or combination of types could be coupled to the LAN 108. In any case, the example controller 102 performs one or more process control routines associated with the system 100 that have been generated by a system engineer and/or other system operator using the application station 106 and which have been downloaded to and/or instantiated in the controller 102.

The example field devices 110, 122, 124, 130 include one or more different sensors to collect different measurements or data associated with operation and/or operating parameters of the asset 128. For example, the field devices 110, 122, 124, 130 of FIG. 1 collect data for the asset 128 related to temperature, pH level, conductivity, sulfide amounts, steam flow, water flow, dew points, pressure, pipe hammer, and/or material thickness. An example of the asset 128 is illustrated below in connection with FIG. 2. The measurements collected by the field devices 110, 122, 124, 130 are passed to the application station 106 via the I/O devices 118, 126, the wireless gateway 123, the application station 134, and/or the controller 102. The example application station 106 uses the measurements to determines when the asset 128 is operating in a potentially corrosive state and/or when the asset 128 is undergoing thermal stress. This potentially corrosive state and/or thermal stress associated with the asset 128 is relayed to an operator via, for example, the operator station 104, to enable the operator to remedy an issue within the asset 128 resulting in corrosion and/or thermal stress. For example, the measurements may be used to detect a potentially corrosive state and/or thermal stress and the operator may be informed of the potentially corrosive state and/or thermal stress. The potentially corrosive state and/or thermal stress may be used to update an overall health of the asset 128. Early detection of corrosion and/or thermal stress using the field devices 110, 122, 124, 130 enables the operator to remedy issues within the asset 128 without and/or before failure of the asset 128, thereby reducing likelihood of production losses and minimizing maintenance costs.

While FIG. 1 illustrates an example system 100 within which the methods and apparatus to assess the condition, health, integrity, and/or performance of an asset (e.g., the asset 128) and/or the likelihood of the onset of potential asset failures (e.g., due to corrosion and/or thermal stress) described in greater detail below may be advantageously employed, the methods and apparatus to control information presented to operators and/or engineers described herein may, if desired, be advantageously employed in other process plants and/or operating process units of greater or less complexity (e.g., having more than one controller, across more than one geographic location, etc.) than the illustrated example of FIG. 1.

Figure 2:
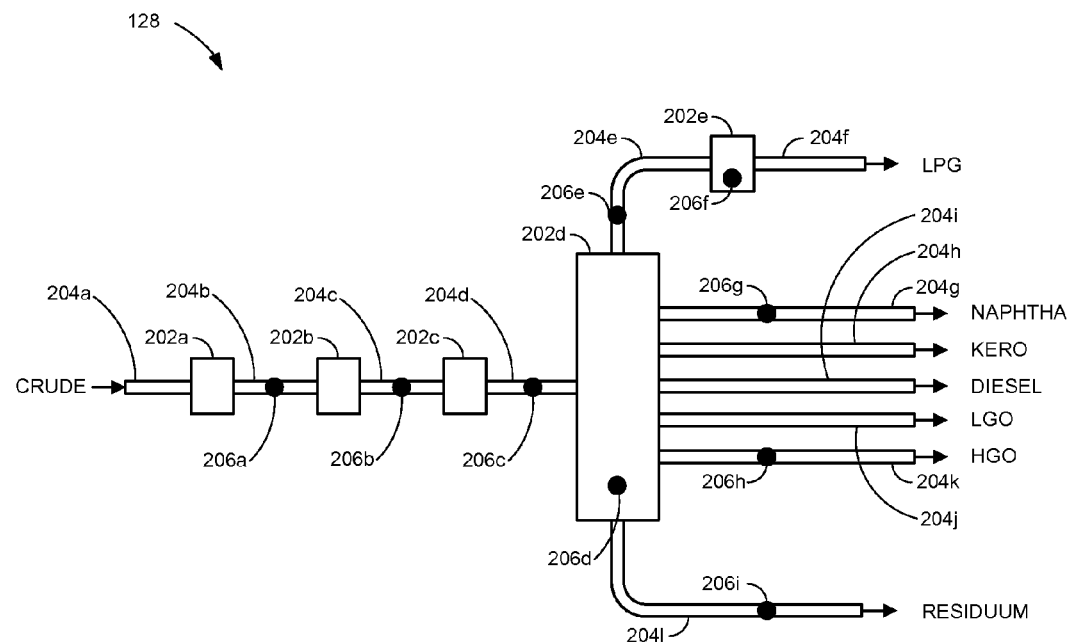
FIG. 2 illustrates an example manner of implementing the example asset of FIG. 1.

FIG. 2 illustrates an example manner of implementing the example asset 128 of FIG. 1. The example asset 128 of FIG. 2 is a liquid hydrocarbon unit (e.g., an atmospheric crude oil fractionation unit). In the example of FIG. 2, the asset 128 includes a plurality of vessels 202a-e (referred to generally as vessels 202) and a plurality of pipe segments 204a-1 (referred to generally as pipe segments 204). In some examples, a single vessel (e.g., the vessel 202a) or a single pipe segment (e.g., the pipe segment 204b) may be referred to as a single asset for monitoring purposes.

In the illustrated example, the example asset 128 passes crude oil through the vessels 202 and pipe segments 204 to form various output materials (e.g., liquefied petroleum gas ("LPG"), naphtha, kerosene, diesel, light gas oil, heavy gas oil, residuum, etc.). The vessel 202a of the illustrated example is a desalter to remove salt from the crude oil passed to the vessel 202a via the pipe segment 204a. The vessel 202b of the illustrated example is a set of heat exchangers to preheat the crude oil passed to the vessel 202b via the pipe segment 204b. The vessel 202c of the illustrated example is an atmospheric heater to heat the crude oil passed to the vessel 202c via the pipe segment 204c. The vessel 202d of the illustrated example is an atmospheric crude distillation unit to form the various output materials from the crude oil passed to the vessel 202d via the pipe segment 204d. The various output materials are output via the pipe segment 204g, pipe segment 204h, pipe segment 204i, pipe segment 204j, pipe segment 204k, and pipe segment 204l. The vessel 202e of the illustrated example is a condenser to condense vapor passed to the vessel 202e via the pipe segment 204e into liquefied petroleum gas output via the pipe segment 204f. Additional or alternative configurations of piping and vessels in a liquid hydrocarbon unit and/or an atmospheric crude oil fractionation unit are possible. For example, heat exchangers (202b) may be located both upstream and downstream of the desalter (202a). In some instances, there may be a flash drum or prefractionation column (not shown) upstream of the crude heater (202c). The systems and methods disclosed herein are not restricted to any particular configuration of assets in the operating process.

The illustrated example includes sensors 206a-i (referred to generally as sensors 206) to monitor the asset 128. Each of the example sensors 206 may correspond to a field device and/or be incorporated into a field device (e.g., the field devices 110, 124, 122, 130 of FIG. 1). The sensors 206 are located at different portions of the asset 128. For example, the sensor 206a monitors the pipe segment 204b and the sensor 206f monitors the vessel 202e. The example sensors 206 monitor the asset 128 and/or operating conditions of the asset 128 and collect measurements such as temperature, pH level, conductivity, sulfide amounts, steam flow, water flow, dew points, pressure, pipe hammer, material thickness, etc. The example sensors 206 include corrosion probes (e.g., including high-temperature probes) to monitor the asset 128 and/or operating conditions of the asset 128. The example sensors 206 collect measurements for the asset 128 continuously, periodically, and/or aperiodically. The period for measurement by the example sensors 206 is set automatically (e.g., to a default setting) and/or selected by an operator. Each of the example sensors 206 may collect one or more measurements.

The example sensors 206 include and/or communicate with transmitters to transmit measurements to I/O devices (e.g., the I/O devices 118, 126 of FIG. 1) and/or wireless gateways (e.g., the wireless gateway 123 of FIG. 1) continuously, periodically, and/or aperiodically. The period for transmitting the measurements is set automatically (e.g., to a default setting) and/or selected by an operator. The measurements are sent to, for example, the application station 106 of FIG. 1 via the wireless gateway 123 and/or the controller 102 of FIG. 1 for use in detecting potential corrosion and/or thermal stress at the asset 128. Corrosion and/or thermal stress may be detected where particular measurements collected by the example sensors 206 are operating above particular thresholds for a period of time.

While the example asset 128 of FIG. 2 includes the sensors 206, any number and/or combination of sensors, transmitters, and/or other devices may be used to implement the asset 128. Furthermore, the sensors 206 may be located on and/or within any component or location of the asset 128 to collect measurements.

Figure 3:
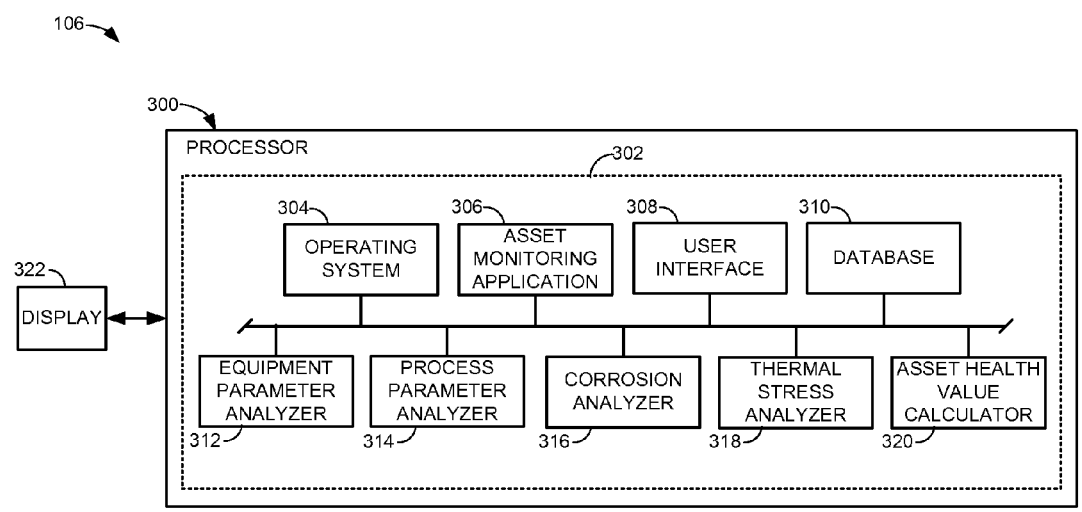
FIG. 3 illustrates an example manner of implementing the example application station of FIG. 1.

FIG. 3 illustrates an example manner of implementing the example application station 106 of FIG. 1. While the following description is provided with respect to the application station 106, the example manner of implementing the example application station 106 may also be used to implement the example operator station 104 of FIG. 1. The example application station 106 of FIG. 3 includes at least one programmable processor 300. The example processor 300 of FIG. 3 executes coded instructions present in a main memory 302 of the processor 300 (e.g., within a random-access memory (RAM) and/or a read-only memory (ROM)). The example processor 300 is any type of processing unit, such as a processor core, a processor, a microcontroller, and/or any type of personal computer (PC). The example processor 300 executes, among other things, an example operating system 304, an example asset monitoring application 306, an example user interface 308, an example database 310, an example equipment parameter analyzer 312, an example process parameter analyzer 314, an example corrosion analyzer 316, an example thermal stress analyzer 318, and an example asset health value calculator 320. The example operating system 304 may be an operating system from, for example, Microsoft®. The example main memory 302 of FIG. 3 may be implemented by and/or within the processor 300 and/or may be one or more memories and/or memory devices operatively coupled to the processor 300.

To allow operators to interact with the example processor 300, the example application station 106 of FIG. 3 includes any type of display 322. Example displays 322 include, but are not limited to, a computer monitor, a computer screen, a television, a mobile device (e.g., a smart phone, a Blackberry™, an iPhone™, and/or an industrial portable PC), etc., capable of displaying user interfaces and/or applications implemented by the processor 300 and/or, more generally, the example operator station 104. The example operating system 304 of FIG. 3 displays and/or facilitates the display of the example user interface 308 associated with the example asset monitoring application 306 by and/or at the example display 322. Aspects of the example user interface 308 are described below in greater detail in connection with FIGS. 4 and 5.

The example asset monitoring application 306 receives measurements (e.g., data) via one or more of the field devices 110, 112, 120, 122, 124, 130 of FIG. 1 and/or sensors 206 of FIG. 2 measuring parameters associated with the operating process unit 101 and/or, more particularly, parameters associated with the operation and/or integrity of assets within the operating process unit 101 (e.g., the example asset 128 of FIGS. 1 and 2). Parameters associated with the condition, state, health, integrity, and/or performance of a piece of equipment (i.e., asset) are herein referred to as equipment parameters. For example, for pipes and vessels (e.g., pipe segments, drums, separators, columns, etc.) equipment parameters may correspond to corrosion rate, wall thickness, pipe hammer, vibration, etc. In the illustrated example, the field devices 110, 112, 122, 124, 130 and/or sensors 206 collect equipment parameters, such as material thickness or metal loss at vessels and/or piping segments (e.g., vessels 202 and/or pipe segments 204 of FIG. 2). Parameters associated with the operation and/or control of an operating process unit, are herein referred to as process parameters. Examples of process parameters include measurements corresponding to parameters such as temperature, pressure, flow rate, composition, etc. In the illustrated example, the field devices 110, 112, 122, 124, 130 and/or sensors 206 collect process parameters, such as pH levels, conductivity, moisture content, pressures, temperatures, flow rates, etc. at the asset 128 (e.g., the vessels 202 and/or the pipe segments 204). In some examples, measured parameters may be relevant to both the condition and/or integrity of an asset as well as the operation and/or control of a process within which the asset is running. For example, the temperature and chemical composition (e.g., pH level) of a liquid in the asset 128 (e.g., at the vessel 202a) may serve as process variables in an operating process unit, and they may also serve as variables used to assess the corrosive impact of the liquid on the asset 128.

The example database 310 of FIG. 3 stores measurements (e.g., data) received via the example asset monitoring application 306 and/or via an operator, which may include laboratory analyses, baseline data and/or limits for equipment parameters as well as weights associated with alarms for the process parameters. The example database 310 stores data associated with corrosivity thresholds and/or thermal stress thresholds used by the example corrosion analyzer 316 and/or the example thermal stress analyzer 318. Additionally, the database 310 may store any of the data output via any of the example equipment parameter analyzer 312, the example process parameter analyzer 314, the example corrosion analyzer 316, the example thermal stress analyzer 318, and/or the example asset health value calculator 320.

In the illustrated example, the example equipment parameter analyzer 312 analyzes measurements (e.g., input data) received via the asset monitoring application 306 that are associated with equipment parameters. To analyze the measurements, the example equipment parameter analyzer 312 determines whether the measurements are valid. For example, a low voltage parameter and/or a "Bad Value" parameter received via the example asset monitoring application 306 may be used to signal whether particular measurements (e.g., inputs) are valid. Validity thresholds may also be used by the example equipment parameter analyzer 312 to determine whether the measurements are valid. Validity thresholds may define particular values (e.g., to be exceeded or not to be exceeded) to qualify the measurements as valid. For example, the corrosion analyzer 316 of FIG. 3 compares a measurement to a validity threshold and, if the measurement exceeds the validity threshold, the equipment parameter analyzer 312 determines that the measurement is invalid. If the measurements are valid, the example equipment parameter analyzer 312 analyzes the measurements. Alternatively, if the measurements are not valid, a health indicator of the asset 128 may be adjusted to indicate a problem or error occurring at the asset affecting the validity of the measurements and/or the ability to determine the corrosive state of the asset.

In the illustrated example, the equipment parameter analyzer 312 compares valid measurements (e.g., the monitored value of each equipment parameter) to a reference value or baseline for the parameter and a preconfigured limit for the parameter to determine if the asset 128 is operating within an acceptable operating window(s). In some examples, the baseline data for an equipment parameter may be defined by an operator, a company expert, industry standards, and/or regulatory codes. In some examples, the equipment parameter analyzer 312 captures the baseline data from measured values of the equipment parameters during operating conditions of the asset 128 where an operator, for example, indicates the asset 128 is operating correctly (e.g., during normal operating conditions). In some examples, the baseline data is captured soon after the asset 128 is configured and first put into operation to reduce the impact of wear and/or degradation in conditions of the asset 128 after extended use. In some instances, the asset 128 has multiple conditions and/or operational states within which it functions. Accordingly, in some such examples, different baseline data may be captured or otherwise defined to be applied for each respective operational state of the asset 128. Furthermore, in some instances, the asset 128 may not have discrete operational states but, instead, may vary depending on some other variable state parameter. For example, corrosion in an asset may vary as a function of the temperature, pressure, flow and composition at which the asset 128 is operating. Thus, the baseline data for corrosion may vary over a range of conditions over which the asset 128 operates. Accordingly, in some examples, where an equipment parameter is dependent on a variable state parameter, a characteristic curve or signature is captured to serve as dynamic baseline data of normal operating conditions for each monitored parameter as a function of the variable state parameter.

In some examples, the limit for an equipment parameter may be defined by an operator, a company expert, industry standards, and/or regulatory codes. In some examples, the equipment parameter analyzer 312 calculates the limit based on the baseline data in accordance with standards guidelines. In some examples, the calculated limit is be further adjusted by a multiplying factor configured by an operator or any other function of operating parameters based on the particular needs and/or operation of the operating process unit.

From the baseline, limit(s), and monitored value of an equipment parameter, the example equipment parameter analyzer 312 calculates a corresponding equipment health value. An equipment health value is a numerical indication of the severity of deviation of a corresponding equipment parameter from its expected value (e.g., its baseline or operating limit). In particular, the equipment health value may indicate the relative position of the equipment parameter within the range between its corresponding baseline and limit(s). In some examples, the health value is related to how far outside a normal operating range a parameter is and how long the parameter has been operating outside of the normal operating range. As different equipment parameters may have different baselines and different limits, in some examples, the equipment health value for each parameter may be normalized such as, for example, by indicating the relative position of the value of the equipment parameter as a percentage along the defined range. In some examples, the percentage may be the complement of the relative deviation from the baseline data. That is, the greater the deviation, the lower the percentage. For example, an equipment parameter with a value at its corresponding baseline (i.e., no deviation) would have an equipment health value of 100% (indicating the asset is operating as expected) while an equipment parameter having a value corresponding to a limit would have an equipment health value of 0%.

In the illustrated example, the process parameter analyzer 314 analyzes measurements (e.g., input data) received via the asset monitoring application 306 that are associated with process parameters. To analyze the measurements, the example process parameter analyzer 314 determines whether the measurements are valid. For example, a low voltage parameter and/or a "Bad Value" parameter received via the asset monitoring application 306 may be used to signal whether particular measurements (e.g., inputs) are valid. Validity thresholds may also be used by the example process parameter analyzer 314 to determine whether the measurements are valid. If the measurements are valid, the example process parameter analyzer 314 analyzes the measurements. Alternatively, if the measurements are not valid, a health indicator of the asset 128 may be adjusted to indicate a problem or error occurring at the asset 128 affecting the validity of the measurements and/or the ability to determine the health state.

In some previous operating process units, process parameters are controlled so that the process parameters substantially maintain values corresponding to a preconfigured set point or point of normal operating conditions (e.g., as defined by baseline data). However, there are times where the parameters may deviate from the set point or where the set points are improperly configured for a given asset operation. Significant deviations may impact the production process and/or create unsafe plant conditions. Accordingly, in the illustrated example, the process parameter analyzer 314 compares valid measurements (e.g., the monitored value of each process parameter) to a reference value or baseline for the parameter and a preconfigured limit for the parameter to determine if the asset 128 is operating within an acceptable operating window.

Process parameters may be assigned one or more alarm limits that may be tripped (i.e., become active) when a corresponding process parameter passes its associated alarm limits. In some examples, the alarm limits are calculated from the baseline data in a similar manner described above for equipment parameters. However, while the significance of equipment parameters depend upon the relative position of the parameter value between its baseline and corresponding limit, process parameters are significant when the parameter value passes the corresponding limit (e.g., an alarm is triggered).

Alarm limits may be configured with differing severity. For example, some alarms may be primarily for informational purposes, while others give warnings, and yet others indicate critical conditions. In the example operating process unit 101, there may be multiple active alarms at any given time, many of which provide the same level of alarm severity (e.g., information, warning, critical, etc.). As such, an operator may be unable to identify among all the alarms that which is most severe or the limiting factor in the process system 100. To overcome this obstacle, the process parameter analyzer 314 in the illustrated example may determine a process health value for each process parameter associated with an active alarm to enable the comparison of the severity of each alarm. A process health value is a numerical indication of the severity or significance of an alarm relative to other alarms. Further, as process health values apply to active alarms (i.e., the corresponding alarms have been triggered), the severity of the alarms indicates the severity of the corresponding issues associated with the asset. More particularly, the example process parameter analyzer 314 determines a process health value corresponding to each process parameter based on a weighting of each alarm associated with each process parameter. For example, every potential alarm corresponding to each process parameter associated with an equipment asset may be weighted on a scale of 0 to 1000 with higher numbers representing more severe alarms. Using only integers, such an example enables up to one thousand alarms to be uniquely ranked or ordered relative to one another according to their severity. In some examples, multiple alarms are assigned the same weight having the same severity. In some examples, the weighting of each alarm is preconfigured for process parameters associated with the asset 128 based on best practices, industry standards, and/or regulatory codes. In some examples, the weighting may be configured and/or adjusted by an operator and/or an expert to enable the operator to isolate and/or focus on alarms of particular interest and/or importance to a particular process or asset.

Additionally, in some examples, the process parameter analyzer 314 may normalize the process health values to the same scale as the equipment health values described above (e.g., reduced to a one hundred point scale or percentage) to enable the comparison of all parameters associated with the asset 128 and to quickly assess the overall health of the asset 128 and/or identify the limiting parameter most affecting the condition and/or performance of the asset 128. The process health values are normalized by reducing the weight of each alarm to a one hundred point scale and then subtracting the weight from 100 (i.e., the complement of the scaled weight). For example, if the 0 to 1000 scale described above is used and a particular alarm is given a weight of 745, the weight is reduced to a 100 point scale by dividing by ten (resulting in 74.5) and then subtracting the result from 100 (resulting in 25.5). Thus, the final process parameter health, expressed as a percentage for comparison with the equipment health values, would be 25.5%.

As described above, some parameters may serve both as an equipment parameter (providing information about the condition, integrity, and/or performance of an asset) and as a process parameter (providing information relevant to the operation and control of a process). Indeed, every parameter may be assigned an alarm limit that is monitored within the operating process unit. For example, in addition to monitoring the position of the value of a corrosion parameter relative to its baseline and limit(s), an alarm limit may also be defined (the same as or different than the limit for the parameter) that triggers an alarm when the limit is exceeded. Such an alarm may be given a weight as with all other alarms and used to calculate a corresponding process health value. Similarly, any monitored parameter may have a baseline and a limit defined and the relative position along the resulting range monitored to calculate an equipment health value.

Additionally, in the illustrated examples, more complex alarms can be defined that are a function of more than one piece of equipment and/or process parameter. In accordance with the teachings of this disclosure, a complex alarm can be created that is triggered only when all conditions are satisfied. Further, this example complex alarm can then be assigned a certain weight to be used in calculating a corresponding process health value. In this manner, operators of then operating process unit 101 can obtain greater insight to assess the overall condition of an asset than is possible using known methods. Furthermore, integrating the analysis of equipment and process parameters in this manner enables operators to predict the likely onset of potential failures earlier on than with known methods, thereby reducing the cost due to downtime and/or maintenance. For example, the occurrence of process operating conditions that cause equipment corrosion can be reduced once the relationships of various parameters are understood and corresponding alarms are configured to alert an operator (e.g., via the operator station 104 of FIG. 1). Without combining all these parameters into an integrated analysis, such a condition and/or the root cause of the condition may go undetected for a significant amount of time.

The example corrosion analyzer 316 of the illustrated example analyzes measurements (e.g., input data) received via the asset monitoring application 306 and analyzed by the example equipment parameter analyzer 312 and/or the example process parameter analyzer 314. The example corrosion analyzer 316 analyzes the measurements to detect a potentially corrosive state of the asset 128.

As described above, more complex alarms may be used that are a function of multiple measurements (e.g., alarms associated with more than one equipment and/or process parameter). In the illustrated example, a corrosivity alarm determined by the example corrosion analyzer 316 is a function of measurements related to one or more of pH levels, conductivity, dew point, temperature, material thickness, asset material, pressure, stream composition, etc. and is dependent on a type of service being performed by the asset. For example, corrosivity alarm parameters may vary based on whether the asset is a liquid hydrocarbon unit (e.g., a crude oil fractionation unit), a gaseous gaseous hydrocarbon unit, an aqueous unit, etc. Integrating the multiple measurements enables operators to predict the likely onset of corrosion earlier than with previous methods, thereby reducing the cost due to downtime and/or maintenance.

A corrosivity index is determined by the example corrosion analyzer 316 based on the measurements collected at the asset as compared to a threshold and/or design operating window. The corrosivity index is a function of the monitored equipment parameters and the process parameters over time. The corrosivity index incorporates (e.g., integrates) different measurements based on, for example, the type of asset implemented (e.g., a liquid hydrocarbon unit, a gaseous gaseous hydrocarbon unit, an aqueous unit, etc.) and material of the asset (e.g., pipe segment 204 material). In the illustrated example, where a liquid hydrocarbon unit (e.g., a crude oil fractionation unit) is implemented as the asset 128, the corrosivity index in a column overhead condenser system is a function of water and/or steam partial pressure, temperature, and time. In some examples the corrosivity index for a pipe in a lower section of the liquid hydrocarbon unit is a function of one or more of flow, temperature, sulfur and acid concentrations in the stream. In some examples, where a gaseous hydrocarbon unit is implemented as the asset 128, the corrosivity index is a function of dew point as determined by the system pressure, temperature, and gas composition, and time. In some examples, where an aqueous unit is implemented as the asset 128, the corrosivity index is a function of pH levels, conductivity, temperature, flow, and time. In determining the corrosivity index, the example corrosion analyzer 316 weights different measurements differently based on the impact of the measurements on a potentially corrosive state. For example, in an aqueous unit, a low pH level may be weighted more significantly in the corrosivity index than a high temperature because a low pH level is more likely to result in a potentially corrosive state. The corrosivity index function for an aqueous unit corresponds to, for example, a Pourbaix diagram which maps out stable phases of an aqueous electrochemical system. The thresholds specify, for example, that a particular pH level is too high based on certain conductivity, temperature, and flow levels, but that same pH level may be acceptable where the conductivity, temperature, and flow levels are different.

The example corrosion analyzer 316 integrates the corrosivity index over time. The corrosivity index is integrated over time because some measurements may extend beyond particular thresholds for an amount of time determined to be insignificant for the corrosion analysis. For example, a temperature that exceeds a threshold for five minutes may not affect the corrosion analysis, but a temperature that exceeds a threshold for five hours may affect the corrosion analysis.

The example corrosion analyzer 316 compares the corrosivity index to thresholds (e.g., corrosion thresholds) to determine the overall health of the asset with respect to corrosion. The thresholds specify limits for the corrosivity index depending on the type of the asset 128 implemented (e.g., a liquid hydrocarbon unit, a gaseous hydrocarbon unit, an aqueous unit, etc.), material of the asset 128 (e.g., a particular iron or other metal composition), wall thickness of the material, and/or desired safety margins.

If the example corrosion analyzer 316 determines that the corrosivity index is above corresponding thresholds for corresponding time periods, the example corrosion analyzer 316 determines that the asset 128 is in a potentially corrosive state and sets a corrosion alarm. The corrosion alarm informs an operator of the potentially corrosive state of the asset 128 and enables the operator to investigate conditions at the asset 128 causing the potentially corrosive state. The corrosion analyzer 316 may also, for example, collect material loss and/or material thickness measurements and compare such measurements to the corrosivity index to verify that potentially corrosive state of the asset 128. A health level for the asset 128 may also be adjusted based on the potentially corrosive state. Example displays associated with corrosion alarms are illustrated in connection with FIGS. 4 and 5.

The example thermal stress analyzer 318 of the illustrated example analyzes measurements (e.g., input data) received via the asset monitoring application 306 and analyzed by the example equipment parameter analyzer 312 and/or the example process parameter analyzer 314. The example thermal stress analyzer 318 analyzes the measurements to determine if the asset 128 is undergoing thermal stress. If the asset 128 is undergoing thermal stress, the example thermal stress analyzer 318 sets a thermal stress alarm.

In the illustrated example, a thermal stress alarm determined by the example thermal stress analyzer 318 is a function of measurements related to one or more of time, temperature, pressure, and asset material. Integrating the multiple measurements enables operators to predict the likely onset of thermal stress earlier on than with previous methods, thereby reducing the cost due to downtime and/or maintenance.

A thermal stress index may be determined by the example thermal stress analyzer 318 based on the measurements collected at the asset. The thermal stress index is a function of changes of the monitored equipment parameters and the process parameters over time. The thermal stress index incorporates (e.g., integrates) different measurements based on, for example, material of the asset, pressure, incidents of temperature gradients (e.g., significant temperature gradients) across pipe segments and/or vessels, incidents of temperature change and how fast such temperature changes occur (e.g., rapid temperature changes). In determining the thermal stress index, the example thermal stress analyzer 318 weights different measurements differently based on the impact of the measurements on potential thermal stress. For example, frequent incidents of large temperature changes may be weighted more significantly in the thermal stress index than a single larger temperature change. The example thermal stress analyzer 318 integrates the thermal stress index over time. The thermal stress index is integrated over time because some measurements may extend beyond particular thresholds for an amount of time determined to be insignificant for the thermal stress analysis.

The example thermal stress analyzer 318 compares the thermal stress index to thresholds (e.g., thermal stress thresholds) to detect potential thermal stress at the asset 128. The thresholds specify limits for measurements based on related measurements depending on the material and/or design of the asset 128 (e.g., a particular iron or other metal composition). The thresholds may specify that a particular pressure associated with a particular temperature change over a particular time period a particular number of times is too high, but that the same pressure for a single temperature change over a longer period of time is acceptable.

If the example thermal stress analyzer 318 determines that the thermal stress index is above corresponding thresholds, the example thermal stress analyzer 318 determines that the asset 128 may be (e.g., has a likelihood of) experiencing thermal stress and sets a thermal stress alarm. The thermal stress alarm informs an operator of the potential thermal stress at the asset 128 and enables the operator to investigate conditions at the asset causing the potential thermal stress. A health level for the asset 128 may also be adjusted based on the potentially corrosive state caused by thermal stress.

The example asset health value calculator 320 in the illustrated example analyzes the equipment and process parameter health values, corrosion alarms, and/or thermal stress alarms associated with the asset 128 in the operating process unit 101 to calculate an asset health value indicative of an overall health or integrity of the asset 128. In some examples, the overall health or integrity of the asset 128 is assumed to be no better than the parameter associated with the asset 128 that exhibits the least or worst health (i.e., the lowest health value). That is, the asset health value calculator 320 generates a value corresponding to the lowest value among all of the equipment health values and the process health values. The asset health value may then be adjusted based on any active corrosion and/or thermal stress alarm.

While an example manner of implementing the example application station 106 of FIG. 1 has been illustrated in FIG. 3, the data structures, elements, processes and devices illustrated in FIG. 3 may be combined, divided, re-arranged, omitted, eliminated and/or implemented in any other way. Further, the example operating system 304, the example asset monitoring application 306, the example user interface 308, the example database 310, the example equipment parameter analyzer 312, the example process parameter analyzer 314, the example corrosion analyzer 316, the example thermal stress analyzer 318, the example asset health value calculator 320, and/or, more generally, the example application station 106 of FIG. 3 may be implemented by hardware, software, firmware and/or any combination of hardware, software and/or firmware. Further still, the example application station 106 may include additional elements, processes and/or devices instead of, or in addition to, those illustrated in FIG. 3, and/or may include more than one of any or all of the illustrated data structures, elements, processes and/or devices.

Figure 4:
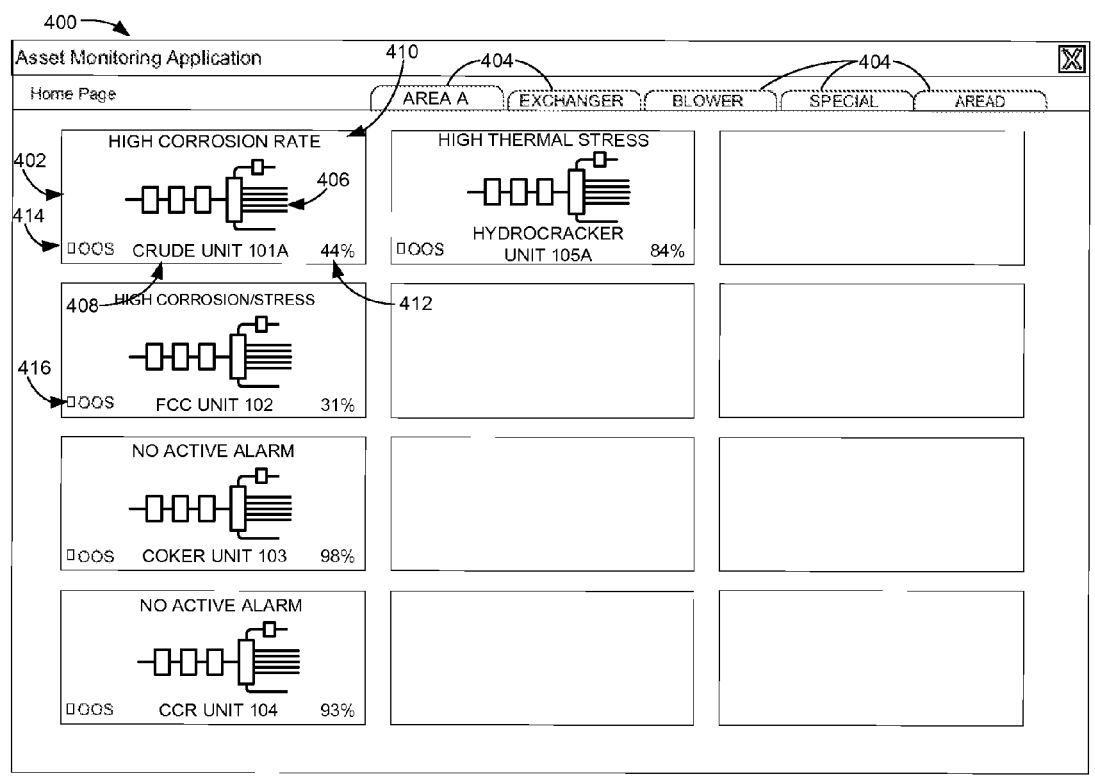
FIG. 4 illustrates an example home page associated with the user interface of FIG. 3.

FIG. 4 illustrates an example overview page or home page 400 associated with the user interface 308 of the asset monitoring application 306 of FIG. 3. In the illustrated example, the home page 400 provides an asset summary graphic 402 for the example operating process unit 101 of FIG. 1. In some examples, the asset summary graphic 402 corresponding to each asset may be grouped by process plant, by process area within a particular process plant, and/or by asset type. Further, the asset summary graphic 402 may be separately rendered via the home page 400 under individual tabs 404 associated with each process plant, process area, and/or asset type. For example, as shown in FIG. 4, the selected tab 404 corresponds to an area (e.g., AREA A) of a process plant and shows five asset summary graphics 402 corresponding to five separate asset types (e.g., a crude oil fractionation unit, a fluid catalytic cracking (FCC) unit, a coker unit, a continuous catalyst regeneration reformer (CCR) unit, and a hydrocracker unit).

Each asset summary graphic 402 provides general information regarding the condition, health, and/or performance of the corresponding asset. Specifically, each asset summary graphic 402 may provide an asset image 406 providing a visual representation of the type of asset (e.g., pump, heat exchanger, compressor, vessel, unit, etc.). Each asset summary graphic 402 may also include a process tag 408 identifying the particular asset associated with its corresponding graphic 402 to which a particular asset summary graphic corresponds. Additionally, in some examples, the asset summary graphic 402 provides a limiting alarm label 410 that identifies the highest weighted active alarm associated with the asset (e.g., a high corrosion rate alarm, a high thermal stress alarm, etc.). As described above, in the illustrated example, a higher weight configured for an alarm is an indication of the severity of the alarm. Thus, the active alarm having the highest weight is an indication of the most serious alarm and, therefore, the limiting alarm corresponding to the particular asset. Furthermore, in some examples, each asset summary graphic 402 provides an indication of the overall health and/or state of the asset by showing an asset health value 412 corresponding to the asset. As discussed above, the asset health value 412 is a numerical indication of the lowest equipment health value or process health value determined for the asset. In the illustrated example, the asset health value 412 is represented as a percentage with one hundred percent (100%) being the best health.

In the illustrated example, the asset health values 412 may change appearance depending on the health value. In some examples, the color of the asset health value 412 may change. For example, values above ninety percent (90%) may be shown in green, values above seventy-five percent (75%) and less than or equal to ninety percent (90%) may be shown in violet, values above fifty percent (50%) and less than or equal to seventy-five percent (75%) may be shown in yellow, and values less than or equal to fifty percent (50%) may be shown in red. Other colors and/or bounds may be implemented as appropriate. Additionally or alternatively, the asset alarm values 412 may flash, increase in intensity, become highlighted, change size, or otherwise change appearance after passing preconfigured thresholds to enable operators to quickly identify the assets in the most critical conditions. Furthermore, other aspects of the asset summary graphic 402 may change appearance along with the asset health value 412 to further draw attention to assets having poor health. For example, each asset summary graphic 402 may be rendered with a border 414 that may change color or appearance in conjunction with the change in color or appearance of the asset health value 412. Further, any other component of the asset summary graphic may change appearance as described above to assist in drawing the attention of an operator based on any suitable threshold(s) predefined for the asset health value 412. In some examples, different types of changes to the appearance of the asset summary graphic 402 may indicate different things. For example, while a change in color may indicate a change in health, a flashing border may indicate one or more unacknowledged alarms associated with the asset. In a similar manner, the label for each tab 404 may also change color to correspond to the lowest asset health value 412 among all assets configured for the process area associated with the tab 404. Additionally or alternatively, the label for each tab 404 may flash when there are unacknowledged alarms associated with any of the assets configured for the corresponding process area.

The asset summary graphic 402 may include an out of service (OOS) checkbox 416. If selected, a command will issue to bring the asset out of service or back into service depending on its current state. When an asset is taken out of service, all alarms become inactive.

Figure 5:
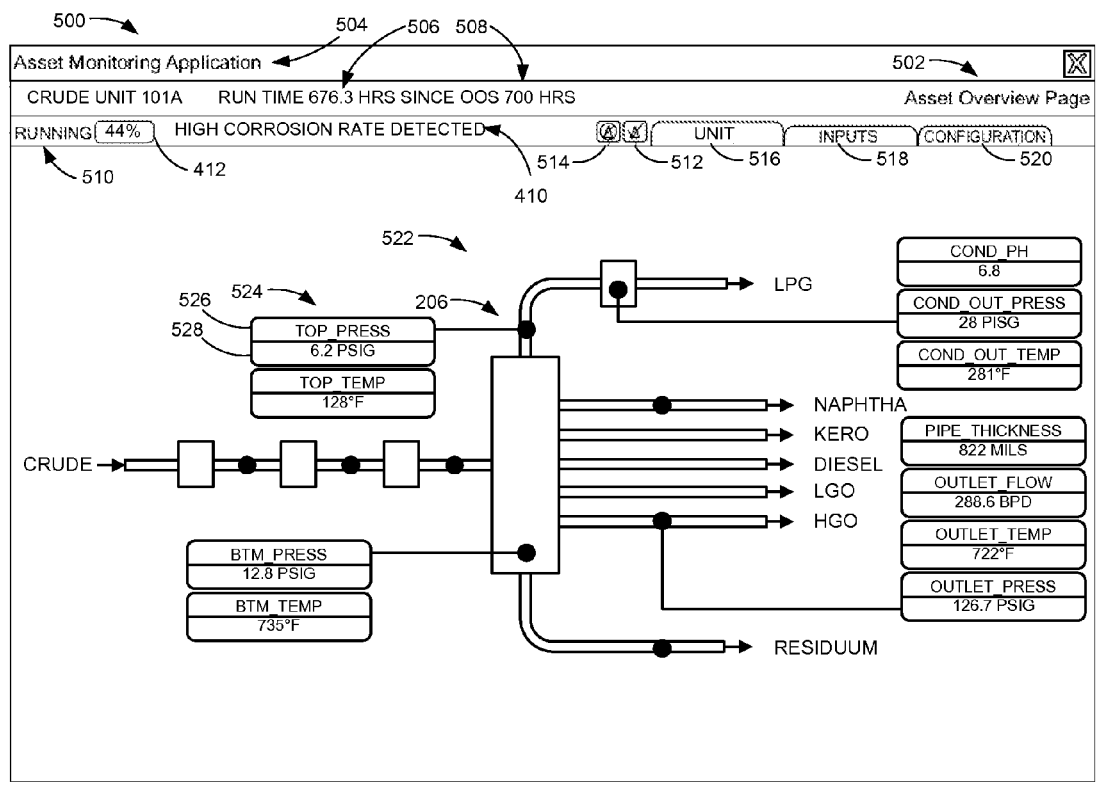
FIG. 5 illustrates an example process tab of an example asset overview page of FIG. 4 associated with the user interface of FIG. 3.

FIG. 5 illustrates an example asset overview page 500 of the user interface 308 of FIG. 3 having multiple sub-views or tabs. Each asset within an operating process unit has a corresponding asset overview page 500 that may be accessed by selecting the corresponding asset summary graphic 402 on the home page 400 of FIG. 4. In the illustrated example, each asset overview page 500 includes a process header 502 that contains basic information associated with the asset such as, a process tag 504, a run time 506 indicating the time since the asset last started running, a total running time 508 since the asset was brought into service, an operating status 510 (e.g., Running/Stopped, Active/Inactive, etc.), an alarm acknowledgement button or icon 512, and a silence horn alarm button or icon 514. The header 502 also includes the asset health value 412 and the limiting alarm label 410 described above in connection with FIG. 4. Furthermore, the appearance (e.g., color) of the asset health value 412 and the limiting alarm label 410 in the header 502 of the example asset overview page 500 corresponds to the appearance described above in connection with FIG. 4.

The example asset overview page 500 may have separate sub-views or tabs including a process tab 516, an inputs tab 518, and a configuration tab 520 that enable an operator to view, access, and/or interact with data related to various aspects of the associated asset. The content of the process tab 516 of the illustrated example provides a process graphic 522 that shows the asset in connection with the relevant components of the process system. The process graphic 522 of the illustrated example corresponds to the asset 128 of FIGS. 1 and 2. Further, the process graphic 522 shows the process variable dynamo 524 for all field inputs installed on the asset along with their position on the asset. The dynamos 524 may be made visible when, for example, a corresponding sensor 206 is selected or rolled-over (e.g., via a pointer or mouse). Each dynamo 524 includes a process tag 526 and a current process parameter value 528 along with corresponding units as read from the field or calculated by the system.

In the illustrated example, each dynamo 524 and/or portions thereof may change in appearance based on data associated with the process system. For example, where an alarm associated with a particular process variable is active and unacknowledged, the process variable may blink at a preconfigured frequency (e.g., at one second intervals). Once acknowledged, in the illustrated example, the blinking stops and the process value may change appearance to indicate the severity of the alarm. In some examples, the process value may change color based on the defined weight of the alarm. For example, if alarms are weighted on a zero (0) to one thousand (1000) scale, informational alarms may correspond to alarm weights from zero (0) to two hundred and fifty (250) and have a violet color, warning alarms may correspond to alarm weights from two hundred and fifty one (251) to four hundred and ninety nine (499) and have a yellow color, and critical alarms may correspond to alarm weights five hundred (500) and above with a red color. If the input signal quality is determined to be bad, in some examples the dynamo 524 may be highlighted or the border change color.

Figure 6:
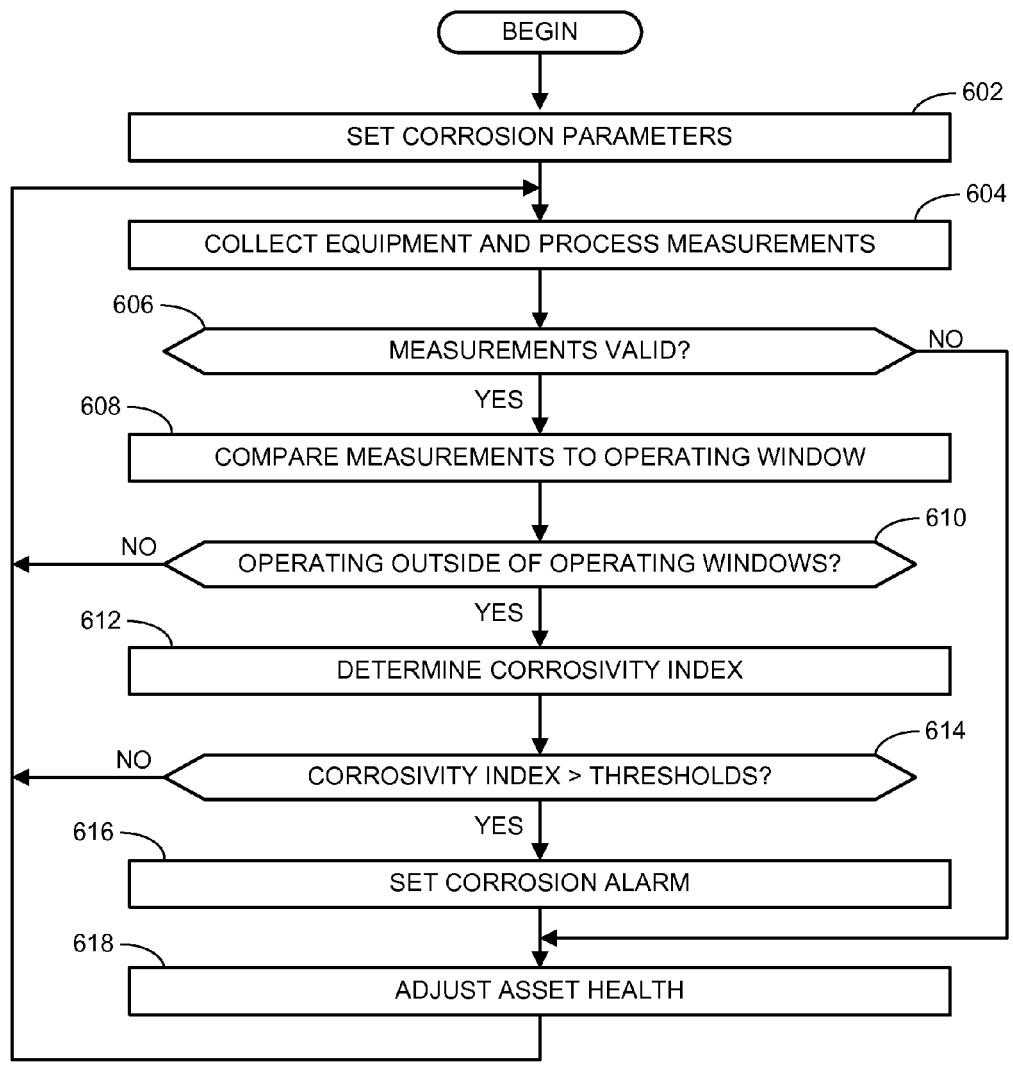
FIG. 6 is a flowchart representative of an example process that may be carried out to implement the example application station of FIGS. 1 and/or 3.
Figure 7:
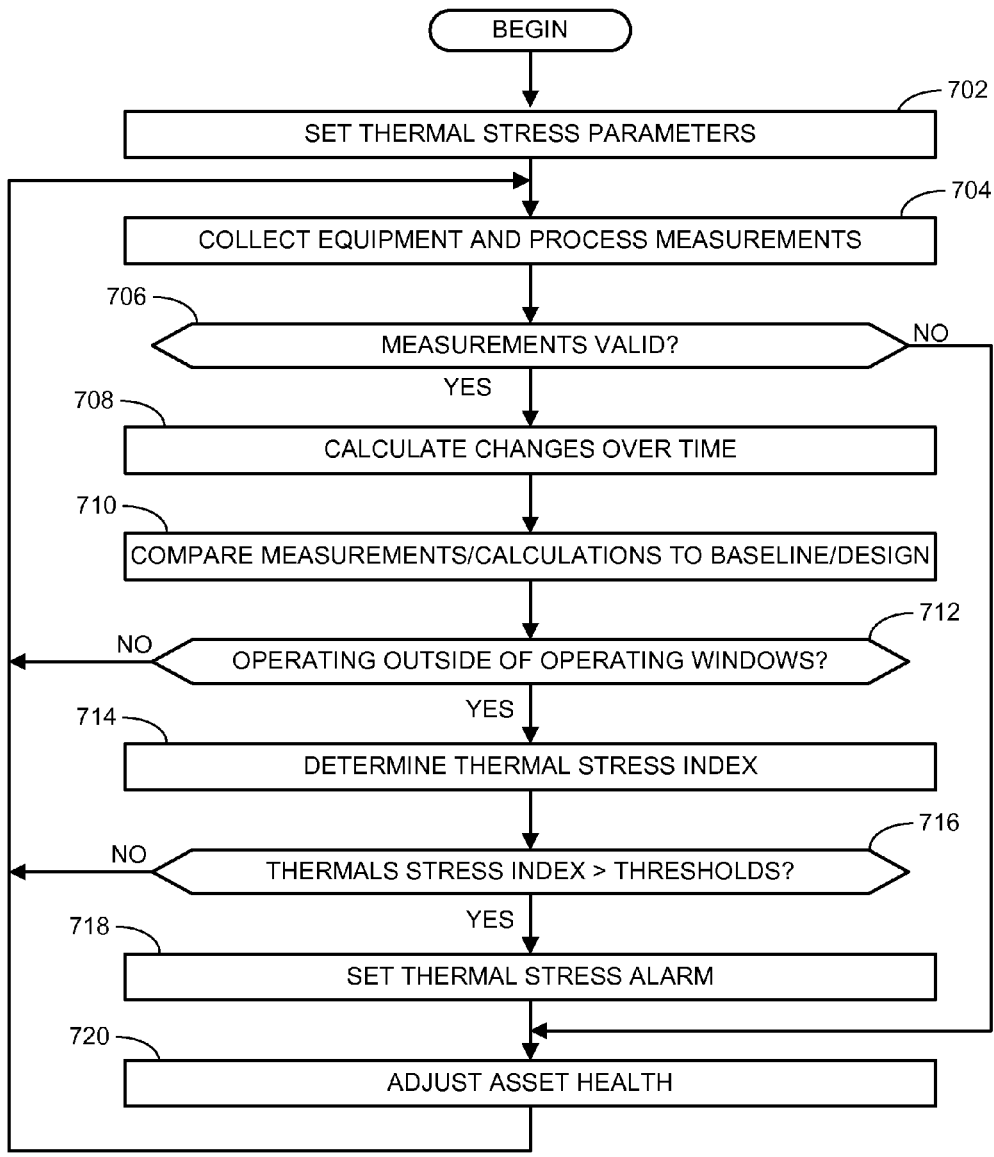
FIG. 7 is a flowchart representative of another example process that may be carried out to implement the example application station of FIGS. 1 and/or 3.

FIGS. 6 and 7 are flowcharts representative of example processes or methods that may be carried out to implement the example application station 106 of FIGS. 1 and/or 2. More particularly, the example methods of FIGS. 6 and/or 7 may be implemented using machine readable instructions that comprise a program for execution by a processor such as the processor 812 shown in the example computer 800 discussed below in connection with FIG. 8. The program may be embodied in software stored on a tangible computer readable storage medium such as a CD-ROM, a floppy disk, a hard drive, a digital versatile disk (DVD), a BluRay disk, or a memory associated with the processor 1312. Alternatively, some or all of the example operations of FIG. 8 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, one or more of the example operations of FIGS. 6 and/or 7 may be implemented manually or as any combination(s) of any of the foregoing techniques, for example, any combination of firmware, software, discrete logic and/or hardware. Further, although the example process is described with reference to the flowcharts illustrated in FIGS. 6 and/or 7, many other methods of implementing the example application station 106 of FIGS. 1 and/or 2 may alternatively be used. For example, the order of execution of the blocks may be changed, and/or some of the blocks described may be changed, eliminated, or combined. Additionally, any or all of the example operations of FIGS. 6 and/or 7 may be performed sequentially and/or in parallel by, for example, separate processing threads, processors, devices, discrete logic, circuits, etc.

As mentioned above, the example methods of FIGS. 6 and/or 7 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example methods of FIGS. 6 and/or 7 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

FIG. 6 is a flowchart representative of an example process that may be carried out to implement the example application station 106 of FIGS. 1 and/or 3. The example process of FIG. 6 begins by setting corrosion parameters for an asset at the example corrosion analyzer 316 (block 602). Corrosion parameters refer broadly to asset settings, measurement settings, alarm settings, etc. Asset settings include, for example, the type of asset implemented (e.g., a liquid hydrocarbon unit, an aqueous unit, a gaseous hydrocarbon unit, etc.), the measurements to be collected for the particular type of asset and/or corrosivity index, thresholds for the particular type of asset, etc. Measurement settings include, for example, validity ranges for the measurement, the frequency at which measurements are collected, the frequency at which collected measurements are to be received (e.g., how often measurements are sent from the field devices 110, 112, 122, 124, 130 of FIG. 1 and/or the sensors 206 to the application station 106), etc. Alarm settings include, for example, when a corrosion alarm is to be activated (e.g., when the corrosivity index exceeds the thresholds), how the corrosion alarm is to be displayed, how the corrosion alarm affects the asset health, etc. The corrosion parameters may be set automatically (e.g., to default values based on asset type) and/or may be set by an operator via the user interface 308 of FIG. 3. The corrosion parameters may be stored in the database 310.

The example application station 106 of FIG. 6 collects equipment and/or process measurements (e.g., parameters) associated with the asset 128 (block 604). The application station 106 of FIGS. 1 and/or 3 collect equipment and/or process measurements from the field devices 110, 112, 120, 122, 124, 130 of FIG. 1 and/or the sensors 206 of FIG. 2. The asset monitoring application 306 passes the equipment and/or process measurements to the equipment parameter analyzer 312 and/or the process parameter analyzer 314 for analysis.

The example method of FIG. 6 then determines if the equipment and/or process measurements are valid (block 606). For example, a low voltage parameter and/or a "Bad Value" parameter received via the asset monitoring application 306 may be used to signal whether particular measurements (e.g., inputs) are valid. Validity thresholds may also be used by the example equipment parameter analyzer 312 and/or the example process parameter analyzer 314 to determine whether the measurements are valid. Validity thresholds may define particular values (e.g., to be exceeded or not to be exceeded) to qualify the measurements as valid. If the measurements are not valid, control proceeds to block 618 and a health indicator of the asset (e.g., an asset health) may be adjusted to indicate a problem or error occurring at the asset affecting the validity of the measurements. If the measurements are valid, the example equipment parameter analyzer 312 and/or the example process parameter analyzer 314 analyzes the measurements.

To analyze measurements, the example method of FIG. 6 compares the measurements (e.g., the valid measurements) to baselines and/or operating windows (block 608). The equipment parameter analyzer 312 and/or the process parameter analyzer 314 compares valid measurements (e.g., the monitored value of each equipment and/or process parameter) to a reference value or baseline for the parameter and a preconfigured limit for the parameter to determine if the asset is operating within an acceptable operating window (block 610). If the asset is not operating outside of the acceptable operating window defined by the reference values/baselines/limits (e.g., the asset is operating within the acceptable operating window), control returns to block 604 and equipment and/or process measurements are collected. If the equipment parameter analyzer 312 and/or the process parameter analyzer 314 determine that the asset is operating outside of the acceptable operating windows with respect to one or more equipment and/or process parameters, the example corrosion analyzer 316 determines a corrosivity index for the asset (block 612).

The corrosivity index incorporates (e.g., integrates) different measurements based on, for example, the type of asset implemented (e.g., a liquid hydrocarbon unit, a gaseous hydrocarbon unit, an aqueous unit, etc.) and/or material composition of the asset. The example corrosion analyzer 316 integrates the corrosivity index over time. The corrosivity index is integrated over time because some measurements may extend beyond particular thresholds for an amount of time determined to be insignificant for the corrosion analysis.

The example method of FIG. 6 compares the current value and the integrated value of the corrosivity index to thresholds to detect a potentially corrosive state at the asset (block 614). The thresholds specify limits for corrosivity depending on, for example, the type of asset implemented (e.g., a liquid hydrocarbon unit, a gaseous hydrocarbon unit, an aqueous unit, etc.), material of the asset (e.g., a particular iron composition), wall thickness of the material, safety margins, asset design, and/or other considerations.

If the example corrosion analyzer 316 determines that the corrosivity index current and integrated values are not above corresponding thresholds for corresponding time periods, control returns to block 604 and equipment and/or process measurements are collected. If the example corrosion analyzer 316 determines that the corrosivity index is above corresponding thresholds for corresponding time periods, the example corrosion analyzer 316 determines that the asset 128 is in a potentially corrosive state and sets a corrosion alarm (block 616). The corrosion alarm informs an operator of the potentially corrosive state of the asset 128 and enables the operator to investigate conditions at the asset 128 causing the potentially corrosive state. The corrosion analyzer may also, for example, collect material loss and/or material thickness measurements and compare such measurements to the corrosivity index to verify that potentially corrosive state of the asset 128. The example corrosion analyzer 316 may increase the severity of the alarm over time if corrosive conditions continue to exist. The example asset health value calculator 320 adjusts a health level for the asset 128 based on the potentially corrosive state (e.g., decreases the asset health) (block 618) as determined by the corrosivity index alarm status and/or severity. Control then returns to block 604 and equipment and/or process measurements are collected.

FIG. 7 is a flowchart representative of another example method that may be carried out to implement the example application station 106 of FIGS. 1 and/or 3. The example method of FIG. 7 begins by setting thermal stress parameters for an asset at the example thermal stress analyzer 318 (block 702). Thermal stress parameters refer broadly to asset settings, measurement settings, alarm settings, etc. Asset settings include, for example, the type of asset implemented (e.g., including asset material), the measurements to be collected for the particular type of asset and/or thermal stress index, thresholds for the particular type of asset, etc. Measurement settings include, for example, the frequency at which measurements are collected, the frequency at which collected measurements are to be received (e.g., how often measurements are sent from the field devices 110, 112, 122, 124, 130 of FIG. 1 and/or the sensors 206 to the application station 106), etc. Alarm setting include, for example, when a thermal stress alarm is to be activated (e.g., when the thermal stress index exceeds the thresholds), how the thermal stress alarm is to be displayed, how the thermal stress alarm will affect the asset health, etc. The thermal stress parameters may be set automatically (e.g., to default values based on asset type) and/or may be set by an operator via the user interface 308 of FIG. 3. The thermal stress parameters may be stored in the database 310.

The example method of FIG. 7 collects equipment and/or process measurements (e.g., parameters) associated with the asset (block 704). The application station 106 of FIGS. 1 and/or 3 collects equipment and/or process measurements from the field devices 110, 112, 120, 122, 124, 130 of FIG. 1 and/or the sensors 206 of FIG. 2. The asset monitoring application 306 passes the equipment and/or process measurements to the equipment parameter analyzer 312 and/or the process parameter analyzer 314 for analysis.

The example method of FIG. 7 determines if the equipment and/or process measurements are valid (block 706). For example, a low voltage parameter and/or a "Bad Value" parameter received via the asset monitoring application 306 may be used to signal whether particular measurements (e.g., inputs) are valid. Validity thresholds may also be used by the example equipment parameter analyzer 312 and/or the example process parameter analyzer 314 to determine whether the measurements are valid. Validity thresholds may define particular values (e.g., to be exceeded or not to be exceeded) to qualify the measurements as valid. If the measurements are not valid, control proceeds to block 720 and a health indicator of the asset 128 (e.g., an asset health) may be adjusted to indicate a problem or error occurring at the asset 128 affecting the validity of the measurements. If the measurements are valid, the example equipment parameter analyzer 312 and/or the example process parameter analyzer 314 analyzes the measurements.

The example method of FIG. 7 calculates changes and/or gradients of the measurements (e.g., the valid measurements) over time across the asset (block 708). The example method of FIG. 7 compares the calculated measurement changes over time and/or the calculated gradients across the asset, to baselines, engineering guidelines, and/or design limits to analyze the measurements (block 710). The equipment parameter analyzer 312 and/or the process parameter analyzer 314 compares valid measurements (e.g., the monitored value of each equipment and/or process parameter) to a reference value or baseline, engineering guidelines, and/or design limits for the parameter and a preconfigured limit for the parameter to determine if the asset 128 is operating within an acceptable operating window (block 712). If the asset 128 is not operating outside of the acceptable operating window defined by the reference values/baselines/limits (e.g., the asset 128 is operating within the acceptable operating window), control returns to block 704 and equipment and/or process measurements are collected. If the equipment parameter analyzer 312 and/or the process parameter analyzer 314 determine that the asset 128 is operating outside of the acceptable operating windows with respect to one or more calculated parameters (e.g., gradients, changes over time, etc.), equipment and/or process parameters, the example corrosion analyzer 316 determines a thermal stress index for the asset 128 (block 714).

The thermal stress index incorporates (e.g., integrates) different measurements based on, for example, material of the asset, pressure incidents, high temperature excursions, large temperature gradients across assets, and/or how fast temperature changes occur. In determining the thermal stress index, the example thermal stress analyzer 318 may weight different measurements differently based on the impact of the measurements on potential thermal stress. For example, a number of incidents of large temperature changes may be weighted more significantly in the thermal stress index than a single larger temperature change. The example thermal stress analyzer 318 integrates the thermal stress index over time. The thermal stress index is integrated over time because repeated occurrences of thermal stress may lead to stress crack corrosion.

The example method of FIG. 7 compares the current and integrated values of the thermal stress index to thresholds to detect thermal stress affecting the asset (block 716). The thresholds specify limits for thermal stress index depending on, for example, one or more of the material of the asset (e.g., a particular iron or other metal composition), wall thickness of the metal, safety margin, etc. The thresholds may specify that a particular temperature change over a particular time period a particular number of times is too high, but that a larger temperature change over a longer period of time is acceptable.

If the example thermal stress analyzer 318 determines that the thermal stress index is not above corresponding thresholds for corresponding time periods, control returns to block 704 and equipment and/or process measurements are collected. If the example thermal stress analyzer 318 determines that the thermal stress index is above corresponding thresholds for corresponding time periods, the example thermal stress analyzer 318 determines that the asset 128 may be experiencing thermal stress and sets a thermal stress alarm (block 718). The thermal stress alarm informs an operator of the potential thermal stress at the asset 128 and enables the operator to investigate conditions at the asset causing the potential thermal stress. The example asset health value calculator 320 adjusts a health level for the asset 128 based on the thermal stress at the asset 128 (e.g., decreases the asset health) (block 720). Control then returns to block 704 and equipment and/or process measurements are collected.

Figure 8:
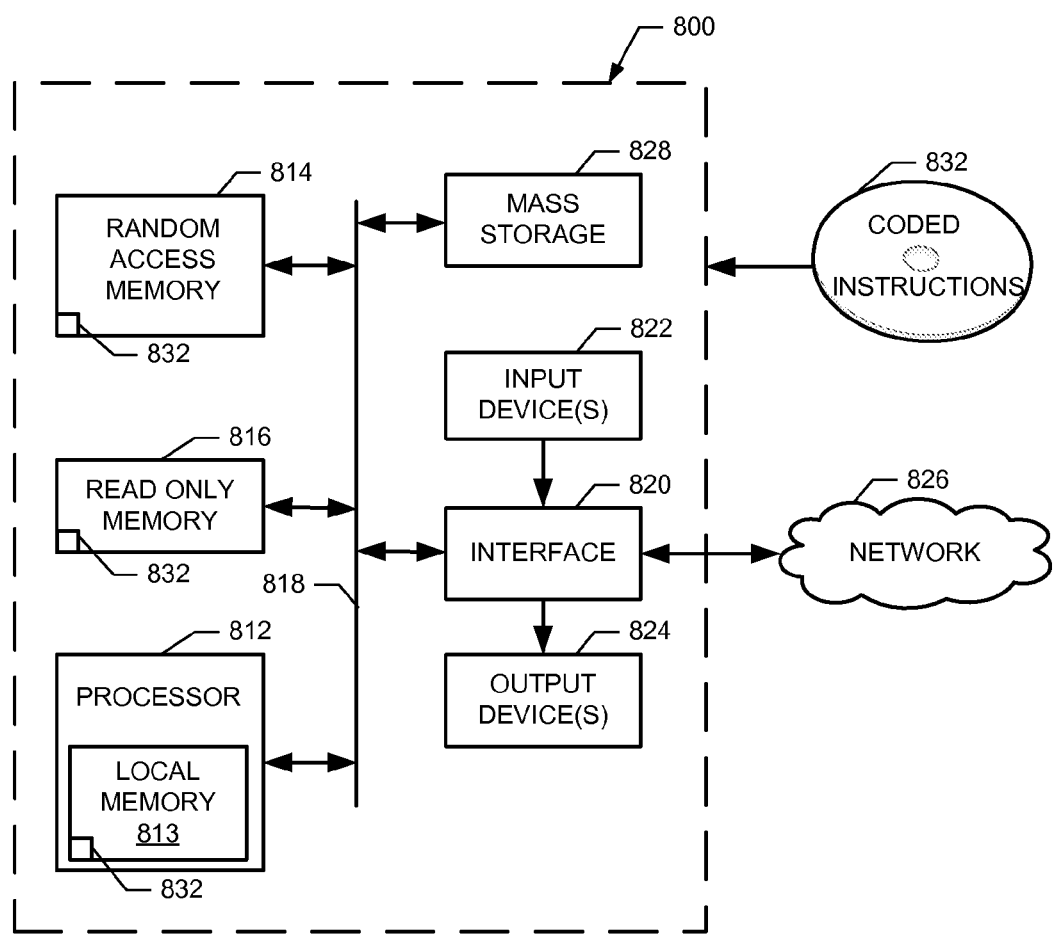
FIG. 8 is a schematic illustration of an example computer that may be used and/or programmed to carry out the example processes of FIGS. 6 and/or 7, and/or, more generally, to implement the example application station of FIGS. 1 and/or 3.

FIG. 8 is a schematic illustration of an example computer 800 that may be used and/or programmed to carry out the example methods of FIGS. 6 and/or 7, and/or, more generally, to implement the asset monitoring application 306, and/or the example application station 106 of FIGS. 1 and/or 3. The computer 800 of the instant example includes a processor 812. For example, the processor 812 can be implemented by one or more microprocessors or controllers from any desired family or manufacturer.

The processor 812 includes a local memory 813 (e.g., a cache) and is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814 and 816 is controlled by a memory controller.

The computer 800 also includes an interface circuit 820. The interface circuit 820 may be implemented by any type of interface standard, such as an Ethernet interface, a universal serial bus (USB), and/or a PCI express interface. One or more input devices 822 are connected to the interface circuit 820. The input device(s) 822 permit a user to enter data and commands into the processor 812. The input device(s) can be implemented by, for example, a keyboard, a mouse, a touchscreen, a track-pad, a trackball, isopoint and/or a voice recognition system. One or more output devices 824 are also connected to the interface circuit 820. The output devices 824 can be implemented, for example, by display devices (e.g., a liquid crystal display, a cathode ray tube display (CRT), a printer and/or speakers). The interface circuit 820, thus, typically includes a graphics driver card.

The interface circuit 820 also includes a communication device such as a modem or network interface card to facilitate exchange of data with external computers via a network 826 (e.g., an Ethernet connection, a digital subscriber line (DSL), a telephone line, coaxial cable, a cellular telephone system, etc.).

The computer 800 also includes one or more mass storage devices 828 for storing software and data. Examples of such mass storage devices 828 include floppy disk drives, hard drive disks, compact disk drives and digital versatile disk (DVD) drives.

Coded instructions 832 to implement the example methods of FIGS. 6 and/or 7 may be stored in the mass storage device 828, in the volatile memory 814, in the non-volatile memory 816, and/or on a removable storage medium such as a CD or DVD.

Although certain example methods, apparatus and articles of manufacture have been described herein, the scope of coverage of this patent is not limited thereto. Such examples are intended to be non-limiting illustrative examples. On the contrary, this patent covers all methods, apparatus and articles of manufacture fairly falling within the scope of the appended claims either literally or under the doctrine of equivalents.

What is claimed is:

1. A method comprising:
monitoring, in substantially real-time, an equipment parameter associated with an asset in an operating process unit;
monitoring, in substantially real-time, a process parameter associated with the asset;
collecting repeated measurements over a period of time from the substantially real-time monitoring of the equipment and process parameters;
comparing the repeated measurements to corresponding corrosion thresholds;
generating an alarm indicative of a potential state of corrosion associated with the asset when the repeated measurements exceed the corresponding corrosion thresholds for corresponding threshold periods of time; and
determining an asset health value corresponding to the asset based on the alarm.

2. The method of claim 1, wherein a value of one of the corrosion thresholds is defined based on an asset type of the asset.

3. The method of claim 2, wherein the asset type is at least one of a liquid hydrocarbon unit, a gaseous hydrocarbon unit, or an aqueous unit.

4. The method of claim 1, further comprising determining the potential state of corrosion by weighting the monitored equipment parameter or the monitored process parameter based on impact on corrosion.

5. The method of claim 1, further comprising determining thermal stress associated with the asset by comparing the repeated measurements to corresponding thermal stress thresholds.

6. The method of claim 5, further comprising creating an alarm associated with the thermal stress when the repeated measurements exceed the corresponding thermal stress thresholds for corresponding threshold periods of time, wherein the alarm is to be presented to an operator.

7. The method of claim 1, further including determining a corrosivity index, wherein the corrosivity index is a function of at least one of current values or changes over time of the equipment parameter and at least one of current values or changes over time of the process parameter.

8. The method of claim 1, further comprising assessing a validity of measurements associated with the monitored equipment parameter or the monitored process parameter, wherein assessing the validity of the measurements includes comparing the measurements to a validity threshold.

9. The method of claim 8, wherein assessing the validity of the measurements includes receiving a low voltage or bad value parameter from an asset monitoring application.

10. The method of claim 1, wherein the potential state of corrosion is detected prior to degradation of the asset.

11. The method of claim 1, wherein a first one of the corrosion thresholds varies depending on whether ones of the repeated measurements exceed a second one of the corrosion thresholds.

12. The method of claim 1, further including monitoring, in substantially real-time, at least one of a second equipment parameter or a second process parameter, wherein generating the alarm is based on the at least one of the second equipment parameter or the second process parameter.

13. A system comprising:
a monitoring application to monitor, in substantially real-time, an equipment parameter and a process parameter associated with an asset in a process unit and collect repeated measurements, over a period of time, from the substantially real-time monitoring of the equipment parameter and the process parameter;
a thermal stress analyzer to compare the repeated measurements for each of the equipment parameter and the process parameter to corresponding thermal stress thresholds and generate an alarm indicative of a thermal stress associated with the asset when the repeated measurements exceed the corresponding thermal stress thresholds for corresponding threshold periods of time; and
an asset health value calculator to determine an asset health corresponding to the asset based on the alarm.

14. The system of claim 13, wherein the thermal stress thresholds are based on at least one of a material composition of the asset, a wall thickness of a material, a safety margin, an engineering guideline, or an industry standard.

15. The system of claim 13, wherein determining the thermal stress includes weighting the monitored equipment parameter and the monitored process parameter based on impact on thermal stress.

16. The system of claim 13, further comprising a corrosion analyzer to determine a potential state of corrosion associated with the asset by comparing the repeated measurements for each of the equipment parameter and the process parameter to corresponding corrosion thresholds.

17. The system of claim 16, wherein the corrosion analyzer is to create an alarm indicative of the potential state of corrosion when the repeated measurements exceed the corresponding corrosion thresholds for corresponding threshold periods of time, wherein the alarm is to be presented to an operator.

18. The system of claim 13, wherein a value of a first one of the thermal stress thresholds corresponding to one of the equipment parameter or the process parameter is defined by a value of at least one of the other one of the equipment parameter or the process parameter, another equipment parameter, or another process parameter.

19. A tangible computer readable storage medium comprising instructions that, when executed, cause a computing device to at least:
monitor, in substantially real-time, an equipment parameter associated with an asset in an operating process unit;
monitor, in substantially real-time, a process parameter associated with the asset;
collect repeated measurements, over a period of time, from the substantially real-time monitoring of the equipment and process parameters;
determine an asset health corresponding to the asset, the asset health being determined based on a potential state of corrosion associated with the asset, the potential state of corrosion determined based on the repeated measurements of the equipment parameter and the repeated measurements of the process parameter;
generate an alarm indicative of the potential state of corrosion associated with the asset when the repeated measurements of the equipment parameter exceed a first corrosion threshold and the repeated measurements of the process parameter exceed a second corrosion threshold; and
adjust the asset health based on the alarm.

20. The computer readable medium of claim 19, wherein a value of one of the corrosion thresholds is defined based on an asset type of the asset.

21. The computer readable medium of claim 19, further comprising instructions that cause the computing device to determine the potential state of corrosion by weighting the monitored equipment parameter and the monitored process parameter based on impact on corrosion.

22. The computer readable medium of claim 19, further comprising instructions that cause the computing device to present the alarm to an operator.

23. The computer readable medium of claim 19, further comprising instructions that cause the computing device to:
determine thermal stress associated with the asset by comparing the repeated measurements to corresponding thermal stress thresholds; and
create an alarm associated with the thermal stress of the asset when the repeated measurements of the equipment parameter exceed a first thermal stress threshold and the repeated measurements of the process parameter exceed a second thermal stress threshold, wherein the alarm associated with the thermal stress is to be presented to an operator.

* * * * *